(12) United States Patent
Petrick et al.

(10) Patent No.: US 6,618,604 B2
(45) Date of Patent: Sep. 9, 2003

(54) METHOD AND APPARATUS FOR CORRECTING THE OFFSET INDUCED BY FIELD EFFECT TRANSISTOR PHOTO-CONDUCTIVE EFFECTS IN A SOLID STATE X-RAY DETECTOR

(75) Inventors: Scott William Petrick, Sussex, WI (US); John Moore Boudry, Waukesha, WI (US); Richard Gordon Cronce, New Berlin, WI (US); Douglas I. Perry, Ottawa (CA)

(73) Assignee: GE Medical Systems Global Technology Company, LLC., Waukesha, WI (US)

( * ) Notice: Subject to any disclaimer, the term of this patent is extended or adjusted under 35 U.S.C. 154(b) by 0 days.

(21) Appl. No.: 09/752,854

(22) Filed: Dec. 28, 2000

(65) Prior Publication Data

US 2002/0087060 A1 Jul. 4, 2002

(51) Int. Cl.⁷ .............................................. A61B 5/058
(52) U.S. Cl. ..................... 600/407; 600/425; 600/473; 600/476; 378/62; 382/128; 250/208.1; 348/308
(58) Field of Search ................................ 600/407, 425, 600/473, 476; 378/62; 382/128; 250/208.1; 348/308, 370.08

(56) References Cited

U.S. PATENT DOCUMENTS

| | | | |
|---|---|---|---|
| 5,099,505 A | * 3/1992 | Seppi et al. | 378/19 |
| 5,117,445 A | * 5/1992 | Seppi et al. | 378/19 |
| 5,168,532 A | * 12/1992 | Seppi et al. | 348/217.1 |
| 5,352,884 A | 10/1994 | Petrick et al. | 250/208 |
| 5,353,884 A | * 10/1994 | Misawa et al. | 175/26 |
| 5,668,375 A | * 9/1997 | Petrick et al. | 250/208.1 |
| 5,692,507 A | * 12/1997 | Seppi et al. | 128/920 |
| 5,920,070 A | * 7/1999 | Petrick et al. | 250/370.09 |
| 6,343,112 B1 | * 1/2002 | Petrick et al. | 378/207 |
| 6,400,798 B1 | * 6/2002 | Leparmentier et al. | 348/362 |

* cited by examiner

Primary Examiner—Marvin M. Lateef
Assistant Examiner—Jeoyuh Lin

(74) Attorney, Agent, or Firm—McAndrews, Held & Malloy, Ltd.; Peter J. Vogel; Michael A. Dellapenna

(57) ABSTRACT

A method and apparatus for correcting the offset induced by Field Effect Transistor (FET) photo-conductive effects in solid state x-ray detectors includes dedicating rows at the beginning and end of an x-ray detector scan. The dedicated rows may be used to measure the "signal" induced by the photo-conductivity of FET switches in solid state x-ray detectors. Since the signal induced by FET photo-conductivity decays over time, the measurements taken at the beginning and end of a detector scan may be used to predict by interpolation the amount of signal contributed by photo-conductive induced offset for each row of the detector scan on a column by column basis.

16 Claims, 5 Drawing Sheets

METHOD AND APPARATUS FOR CORRECTING THE OFFSET INDUCED BY FIELD EFFECT TRANSISTOR PHOTO-CONDUCTIVE EFFECTS IN A SOLID STATE X-RAY DETECTOR

CROSS REFERENCE TO RELATED APPLICATIONS (if applicable)

Not applicable.

STATEMENT REGARDING FEDERALLY SPONSORED RESEARCH & DEVELOPMENT (if applicable)

Not Applicable.

BACKGROUND OF THE INVENTION

The present invention generally relates to medical diagnostic imaging systems, and in particular relates to a method and apparatus for correcting the digital image offset induced by Field Effect Transistor (FET) photo-conductive effects in medical imaging systems employing solid state detectors.

X-ray imaging has long been an accepted medical diagnostic tool. X-ray imaging systems are commonly used to capture, as examples, thoracic, cervical, spinal, cranial, and abdominal images that often include information necessary for a doctor to make an accurate diagnosis. X-ray imaging systems typically include an x-ray source and an x-ray sensor. When having a thoracic x-ray image taken, for example, a patient stands with his or her chest against the x-ray sensor as an x-ray technologist positions the x-ray sensor and the x-ray source at an appropriate height. X-rays produced by the source travel through the patient's chest, and the x-ray sensor then detects the x-ray energy generated by the source and attenuated to various degrees by different parts of the body. An associated control system obtains the detected x-ray energy from the x-ray sensor and prepares a corresponding diagnostic image on a display.

The x-ray sensor may be a conventional screen/film configuration, in which the screen converts the x-rays to light that exposes the film. The x-ray sensor may also be a solid state digital image detector. Digital detectors afford a significantly greater dynamic range than conventional screen/film configurations.

One embodiment of a solid state digital x-ray detector may be comprised of a panel of semiconductor FETs and photodiodes. The FETs and photodiodes in the panel are typically arranged in rows (scan lines) and columns (data lines). A FET controller controls the order in which the FETs are turned on and off. The FETs are typically turned on, or activated, in rows. When the FETs are turned on, charge to establish the FET channel is drawn into the FET from both the source and the drain of the transistor. The source of each FET is connected to a photodiode. Each photodiode integrates the light signal emitted by the scintillator above it in response to the absorption of x-rays and discharges energy in proportion to the x-rays absorbed. The gates of the FETs are connected to the FET controller. The Image Acquisition Module reads signals discharged from the panel of FETs and photodiodes. The Image Acquisition Module converts the signals discharged from the panel of FETs and photodiodes. The converted energy discharged by the photodiodes in the detector is used by the Image Acquisition Module to activate pixels in the displayed digital diagnostic image. The panel of FETs and photodiodes is typically scanned by row. The corresponding pixels in the digital diagnostic image are typically activated in rows.

The FETs in the x-ray detector act as switches to control the charging and discharging of the photodiodes. When a FET closes, an associated photodiode is recharged to an initial charge. While the FETs are open, the photodiodes are bombarded with x-rays. The number of x-rays experienced by each photodiode corresponds to the x-ray dose. The x-rays are absorbed by the scintillator above the photodiode, which emits light and discharges the photodiodes in contact therewith. Thus, after the conclusion of the exposure, while the FETs are open, the photodiodes retain a charge representative of the x-ray dose. When a FET is closed, a certain amount of charge is applied thereto in order to re-establish a desired charge across the photodiode. When a FET is closed, the amount of charge required to restore the initial charge on each photodiode is measured. The measured charge amount becomes a measure of the x-ray dose integrated by the scintillator, with the resulting light integrated by the photodiode during the length of the x-ray exposure.

X-ray images may be used for many purposes. For instance, internal defects in a target object may be detected. Additionally, changes in internal structure or alignment may be determined. Furthermore, the image may show the presence or absence of objects in the target. The information gained from x-ray imaging has applications in many fields, including medicine and manufacturing.

In any imaging system, x-ray or otherwise, image quality is of primary importance. In this regard, x-ray imaging systems that use digital or solid state image detectors ("digital x-ray systems") face certain unique difficulties. In particular, digital x-ray systems must meet stringent demands on Critical to Quality (CTQ) measurements in order to provide a usable image. CTQ measurements include image resolution, image resolution consistency (e.g., comparing an image from one system to another system), and image noise (artifacts, "ghosts," or distortions in the image). In the past, however, digital x-ray systems were often unable to meet CTQ requirements or provide consistent image quality. This deficiency in part may be due to process variations in the semiconductor fabrication techniques used to manufacture solid state digital image detectors. Additionally, the decrease in image quality may be due to the inherent charge retention properties of semiconductor materials used in imaging technology.

Many semiconductor devices exhibit photo-conductive characteristics. Photo-conductivity is an increase in electron conductivity of a material through optical (light) excitation of electrons in the material. Photo-conductive characteristics are exhibited by the FETs used as switches in solid state x-ray detectors. Ideally, FET switches isolate the photodiode from the electronics which measure the charge restored to the photodiode. FETs exhibiting photo-conductive characteristics do not isolate the photodiode from the system, when the FETs are open. Consequently, charge from multiple photodiodes is restored simultaneously by the Image Acquisition Module. The Image Acquisition Module can not distinguish to which photodiodes the charge is restored, which corrupts the image acquisition process. The unintended charge leakage through the FETs may produce artifacts or ghost images or may add a charge offset to component values in the digital x-ray image.

FETs and other materials made of amorphous silicon also exhibit a characteristic referred to as charge retention. Charge retention is a structured phenomenon and may be controlled to a certain extent. Charge retention corresponds to the phenomenon whereby not all of the charge drawn into the FET to establish a conducting channel is forced out when the FET is turned off. The retained charge leaks out of the FET over time, even after the FET is turned off, and the leaked charge from the FET adds an offset to the signal read out of the photodiodes by the x-ray control system.

The FETs in the x-ray detector exhibit charge retention characteristics when voltage is applied to the FETs to read the rows of the x-ray detector. The detector rows are generally read in a predetermined manner, sequence, and time interval. The time interval may vary between read operations for complete frames of the x-ray image. When a FET is closed, the charge on an associated photodiode is restored by a charge measurement unit but the FET retains a portion of the charge. When the FETs are opened, between read operations, a portion of the charge retained by the FETs leaks from the FETs to a charge measurement unit. The amount of charge that leaks from the FETs exponentially decays over time. The next read operation occurs before the entire retained charge leaks from the FETs. Consequently, the charge measurement unit measures during each read operation an amount of charge that was retained by the FETs during the previous read operation.

The charge remaining on the FETs when a new read operation is initiated is referred to as the initial charge retention. The initial charge retention stored on multiple FETs, such as the FETs of a single row of column, combines to form a charge retention offset. The charge retention offset varies based on the rate at which rows of the x-ray detector panel are read. As the interval increases between read operations, the charge decay increases. When the panel rows are read at a constant rate, the charge retention offset builds to a steady state value. The steady state value for the charge retention rate represents the point at which the panel rows are read at a rate equaling the exponential decay rate of the charge on the FETs.

If the times between frames for both the offset and x-ray image are consistent, the effect of charge retention may be eliminated from the final image. In the normal process of reading a detector, the effect of retained charge may be minimized, during calibration, by simply subtracting the results of a "dark" scan from the results of an "exposed" scan. A "dark" scan is a reading done without x-ray exposure. A "dark" scan simply activates the FETs on the x-ray detector panel. Thus, a "dark" scan may determine the charge retention characteristics exhibited by the FETs activated to read the x-ray detector. By subtracting the "dark" scan from the actual "exposed" scan of a desired object, the charge retention effects may be eliminated.

During an x-ray exposure, a similar phenomenon occurs whereby charge is generated in the FET as a result of the FET photo-conductive characteristics. When the FETs are turned off at the end of the exposure, the additional charge also leaks out and adds to the read signal in a manner analogous to charge retention. However, the additional charge cannot be removed because the additional charge resulting from the FET photo-conductive characteristics relates to the x-rays bombarding the x-ray detector. Thus, the additional charge resulting from the FET photo-conductive characteristics is not predictable or nor is it reproducible in a "dark" image where no x-rays are transmitted. The number of FETs that photo-conduct and the amount of charge conducted by the FETs are dependent upon the amount of x-ray exposure and the object imaged, as well as upon the individual properties of each FET. Since a solid state x-ray detector is structured along rows (scan lines) and columns (data lines), the excess charge in the FETs may result in structured image artifacts or offsets which cannot be corrected by contrasting the "exposed" image with a "dark" image.

Photo-conductivity is not as structured as charge retention. First, when a FET in the x-ray detector is turned on to be read, the FET is always turned on with the same voltage. With the photo-conductive effect, the "amount" that the FET is turned on is determined by the intensity of the light reaching a given FET. The light reaching the FETs may vary among a wide range of intensities for all of the FETs on the x-ray detector. Second, regardless of how strongly each FET is affected by photo-conductivity (due to the light intensity at each FET), all of the FETs will be affected simultaneously. Charge retention only stimulates one FET in any given column at a time. Therefore, photo-conductivity is much more unpredictable and is uncorrectable by a simple image subtraction method.

As noted above, the characteristics of digital image detectors inherently vary. Although there is a need to provide consistent image quality (and in particular, image resolution) within and across multiple medical diagnostic imaging systems, there has been in the past no automated technique for providing such consistency. Furthermore, the stringent CTQ requirements may result in low acceptable yields for digital image detectors which are then destroyed, or, at best, deemed unusable for medical diagnostic systems. Consequently, time, money, and resources are wasted.

Thus, a need exists for a method and apparatus for correcting the offset induced by Field Effect Transistor photo-conductive effects in a solid state x-ray detector.

BRIEF SUMMARY OF THE INVENTION

A preferred embodiment of the present invention provides a method and apparatus for correcting the digital image offset induced by Field Effect Transistor (FET) photo-conductive effects in solid state x-ray detectors. The method and apparatus include adding one or more rows to both the beginning and end of a normal x-ray detector scan area. The additional rows may be outside the physical image area of a solid state x-ray detector. The additional rows then may be used to measure the "signal" induced by the photo-conductivity of FET switches in a solid state x-ray detector. The signal may be measured at both the beginning and end of a detector scan. Since the signal induced by FET photo-conductivity decays over time, the measurements taken at the beginning and end of a detector scan may be used to predict by interpolation the amount of signal contributed by photo-conductive induced offset for each row of the detector scan on a column by column basis.

An alternative preferred embodiment may use an existing solid state x-ray detector scan area and simply not activate one or more rows at the beginning and end of the x-ray detector scan area. This embodiment may reduce the image area covered by the scan.

DETAILED DESCRIPTION OF THE INVENTION

Figure 1:
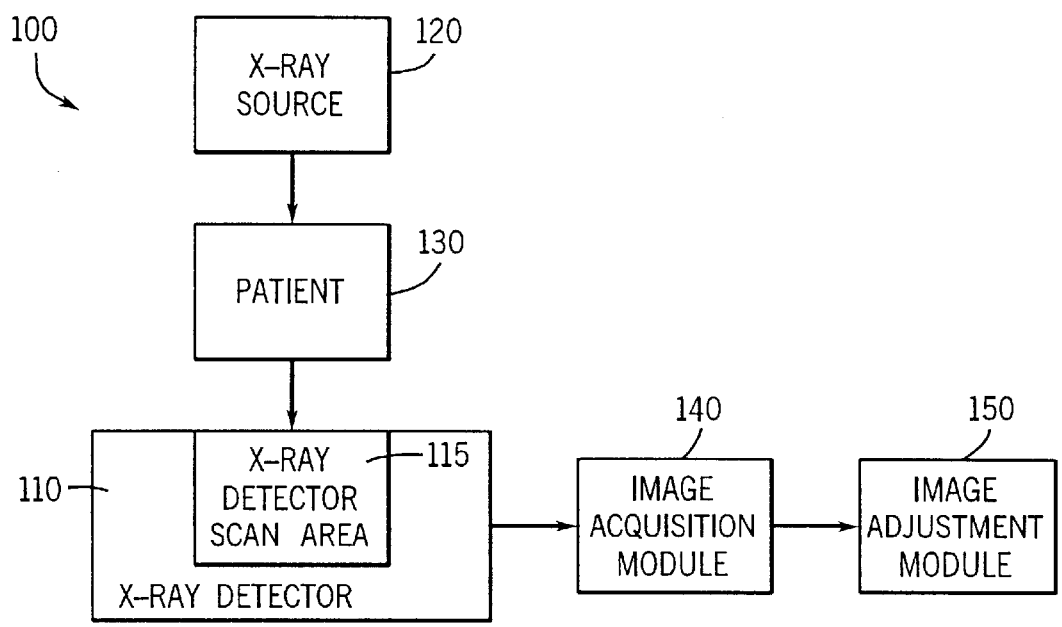
FIG. 1 illustrates a preferred embodiment of a general medical diagnostic imaging system used in connection with the present invention.

FIG. 1 illustrates a preferred embodiment of a medical diagnostic imaging system 100 used in accordance with the present invention. The medical diagnostic imaging system 100 includes a plurality of subsystems. For the purposes of illustration only, the medical diagnostic imaging system is described as an x-ray system. The medical diagnostic imaging system 100 includes subsystems, such as an x-ray detector 110, an x-ray detector scan area 115, an x-ray source 120, and a patient 130. The medical diagnostic imaging system 100 also includes an image acquisition module 140 and an image adjustment module 150.

The patient 130 is positioned in the medical diagnostic imaging system 100. In one exemplary system, an x-ray source 120 is positioned above the patient 130. The x-ray detector 110 is positioned below the patient 130. X-rays are transmitted from the x-ray source 120 through the patient 130 to the x-ray detector 110 and the x-ray detector scan area 115.

Figure 4:
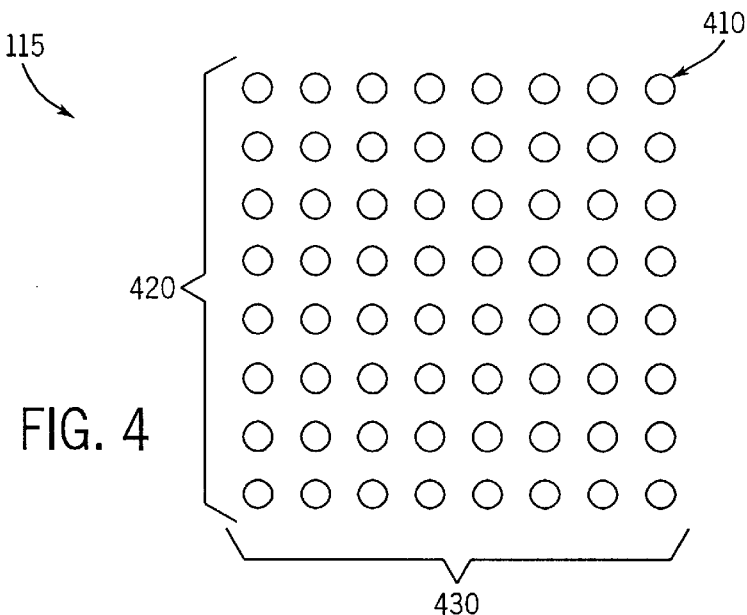
FIG. 4 illustrates a preferred embodiment of a solid state x-ray detector.

FIG. 4 illustrates a preferred embodiment of a solid state x-ray detector scan area 115 within an x-ray detector 110. The x-ray detector scan area 115 is comprised of cells 410 corresponding to pixels in an x-ray image. Each cell 410 typically comprises a photodiode and a Field Effect Transistor (FET). The cells 410 may be arranged in columns (data lines) 420 and rows (scan lines) 430. The cells 410 are activated by row 430 and by column 420. One or more cells 410 are uniquely mapped to one or more pixels in an x-ray image. The pixels are activated to produce the desired digital x-ray image of the patient 130.

Figure 7:
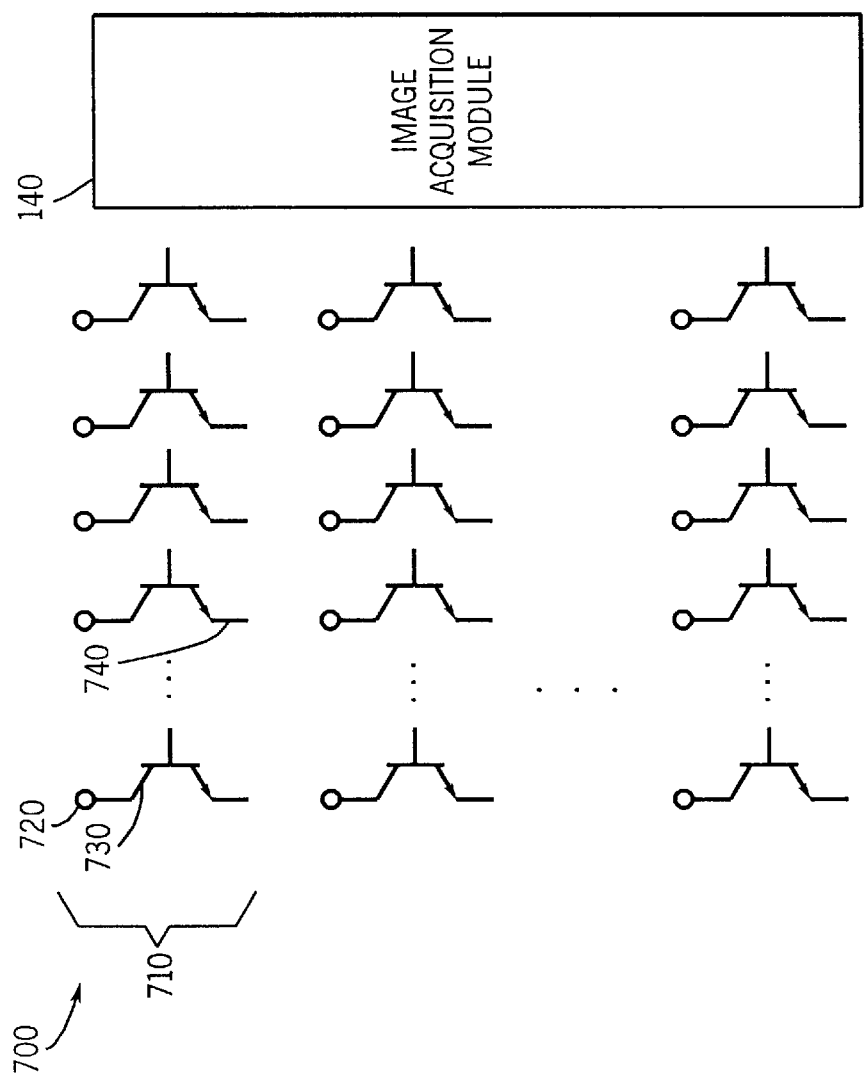
FIG. 7 illustrates a preferred embodiment of a solid state x-ray detector scan.

FIG. 7 illustrates a lower-level view of a preferred embodiment of a solid state x-ray detector scan area 115 within an x-ray detector 110. The x-ray detector scan area 115 is comprised of cells 710 comprising a photodiode 720 and a Field Effect Transistor (FET) 730. Leads 740 connect the cells 710 to the image acquisition module 140.

Figure 5:
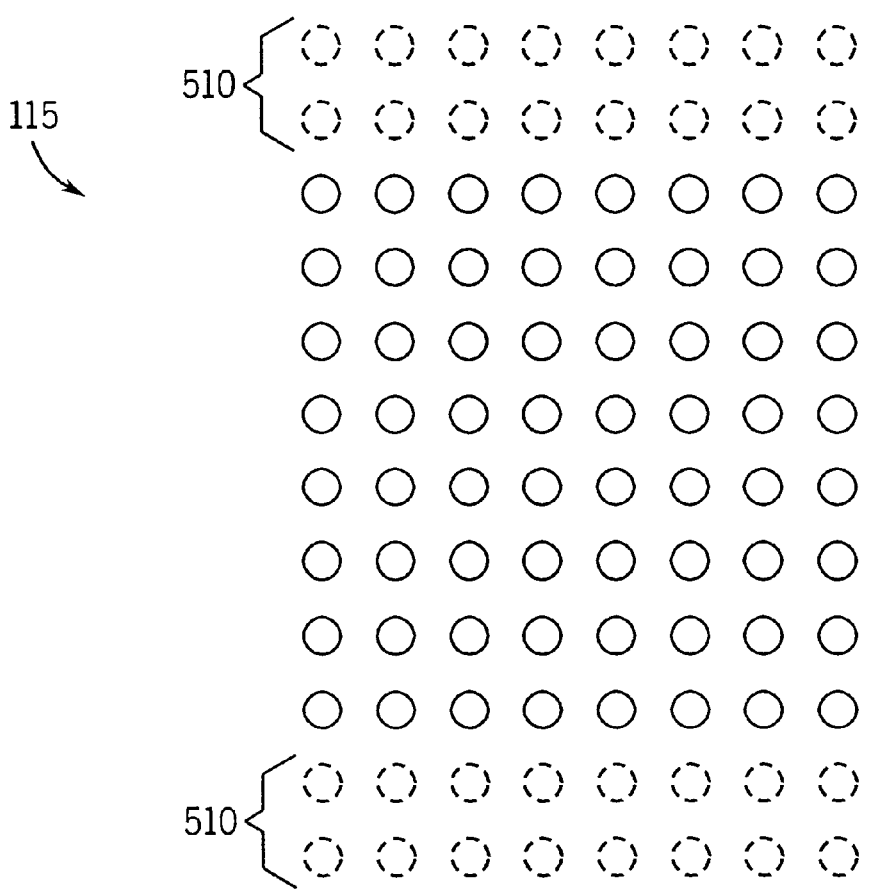
FIG. 5 illustrates a preferred embodiment of a solid state x-ray detector scan area with two additional rows for offset correction at the beginning of the x-ray detector scan area and two additional rows for offset correction at the end of the x-ray detector scan area.

The image acquisition module 140 acquires an x-ray image from the x-ray detector scan area 115. In a preferred embodiment, the image acquisition module 140 may acquire an image from an area, an exposed detector section, larger than the normal patient subsection of the x-ray detector scan area 115. In a preferred embodiment, shown in FIG. 5, the x-ray detector scan area 115 may be enlarged by scanning additional rows 510 before the beginning of the x-ray detector scan area 115 or scanning additional rows 510 after the end of the x-ray detector scan area 115 to form an enlarged x-ray detector scan area 115. The number of rows 510 may vary. Also, the rows 510 may be located along one of both sides of the x-ray detector scan area 115, in addition to or in place of being located before and after the x-ray detector scan area 115. The image acquisition module 140 may acquire the image from the enlarged x-ray detector scan area 115.

Figure 6:
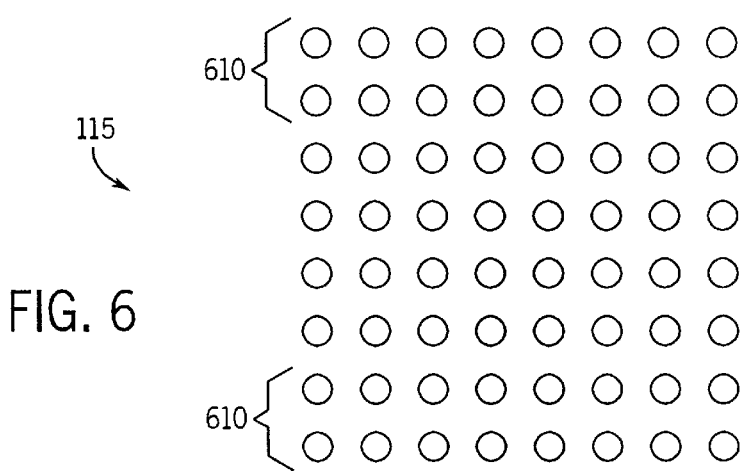
FIG. 6 illustrates a preferred embodiment of a solid state x-ray detector scan area with two rows dedicated for offset correction at the beginning of the x-ray detector scan area and two rows dedicated for offset correction at the end of the x-ray detector scan area.

In another preferred embodiment, shown in FIG. 6, the x-ray detector scan area 115 may be reduced by one or more rows 610 at the beginning of the x-ray detector scan area 115 and one or more rows 610 at the end of the x-ray detector scan area 115 and/or one or more rows along either side of the x-ray detector scan area 115. The rows dedicated in the normal x-ray detector scan area 115 may be used for offset correction in place of the additional rows 510 added in another preferred embodiment. The image acquisition module 140 may acquire an x-ray image from the x-ray detector scan area 115.

The image acquisition module 140 may acquire an x-ray image from the x-ray detector scan area 115 by receiving a signal from the leads 740 from the cells 410, 710 in the x-ray detector scan area 115. The signal from the leads 740 may be generated by charge stored in the photodiodes 720. The charge stored in the photodiodes 720 may result from absorption of x-ray energy by the photodiodes 720. The FETs 730 allow the charge stored in the photodiodes 720 to travel as a signal through the leads 740. The FETs 730 may be actuated by the image acquisition module 140. The signal received by the image acquisition module 140 through the leads 740 may include an offset produced by the charge retention characteristics and photo-conductive effects of the FETs 730.

The image adjustment module 150 receives the acquired image from the image acquisition module 140. The image adjustment module 150 corrects the offset induced in the image by the x-ray detector 110. The offset in the x-ray image may be induced by the photo-conductive and/or charge retention properties of the FETs (Field Effect Transistors) 730 in the x-ray detector 110. In a preferred embodiment, the charge retention offset from the FETs 730 may be eliminated using a "dark" image containing the charge leakage caused by charge retention in the FETs. In a preferred embodiment, the additional rows scanned at the beginning and end of the x-ray detector scan area 115 are utilized by the image adjustment module 150 to correct the offset induced by FET photo-conductive effects in the x-ray image. In an alternative preferred embodiment, the rows dedicated at the beginning and end of the normal x-ray detector scan area 115 are utilized by the image adjustment module 150 to correct the offset induced by FET photo-conductive effects in the x-ray image.

Figure 2:
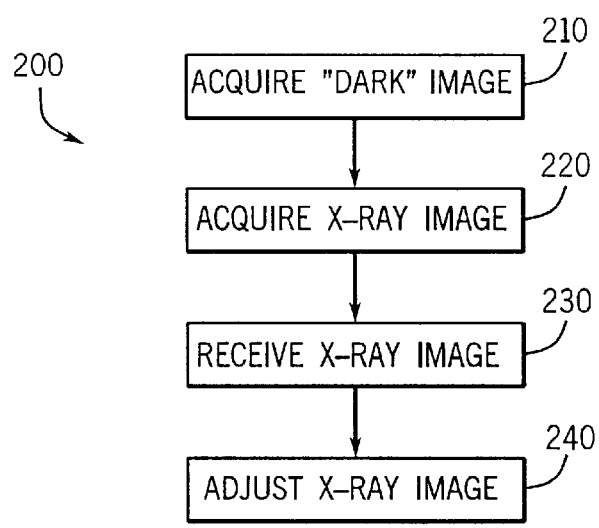
FIG. 2 illustrates a flow diagram of a preferred embodiment for correcting the offset induced by FET (Field Effect Transistor) photo-conductive effects in a solid state x-ray detector.

Turning now to FIG. 2, the figure illustrates a flow diagram 200 for a preferred embodiment for correcting the offset induced in a medical diagnostic imaging system according to the present invention. In step 210, the image acquisition module 140 acquires a "dark" image from the x-ray detector scan area 115. A "dark" image is obtained from a reading done without an x-ray exposure. A scan for a "dark" image activates the FETs 730 in the x-ray detector scan area 115 and measures retained charge leakage from the FETs 730. Thus, a "dark" image may be used to determine the charge retention offset produced by the FETs 730 activated to read the x-ray detector scan area 115.

In step 220, the image acquisition module 140 acquires an x-ray image from the x-ray detector scan area 115. The image is offset by excess charge from sources such as the photo-conductive effects and charge retention characteristics of FETs 730 comprising the solid state x-ray detector 110. The x-ray image is read row by row by the image acquisition module 140 from the x-ray detector scan area 115 using leads 740 from cells 710 in the x-ray detector scan area 115. In a preferred embodiment of the present invention, the image acquisition module 140 acquires two additional rows 510 at the beginning of the image scan and also acquires two additional rows 510 at the end of the image scan. The additional rows 510 do not represent the object being scanned. The additional rows 510 indicate the offset charge "signal" that is induced by FET photo-conductive effects. In another preferred embodiment of the present invention, the image acquisition module 140 dedicates two rows 610 at the beginning of the x-ray detector scan area 115 and two rows 610 at the end of the x-ray detector scan area 115 to photo-conductivity measurement, thus reducing the overall size of the acquired image.

During operation, the image acquisition module 140 performs consecutive or successive scans (read operations) of each row 430 of cells 410, 710 in the x-ray detector scan area 115. First, the image acquisition module 140 scans one or more rows 510, 610 outside (e.g., before) the scanned image area of the x-ray detector scan area 115. The image acquisition module 140 acquires photo-conductive offset data from the rows 510, 610 scanned outside the scanned image area of the x-ray detector scan area 115. The image acquisition module 140 then performs a row by row scan of each row 430 in the scanned image area of the x-ray detector scan area 115. During the row by row scan of each row 430 in the scanned image area of the x-ray detector scan area 115, the image acquisition module 140 obtains exposure data for each cell 410, 710 in the x-ray detector scan area 115. The image acquisition module 140 then may scan one or more other rows 510, 610 outside (e.g., after) the scanned image area of the x-ray detector scan area 115. The image acquisition module 140 acquires photo-conductive offset data from the rows 510, 610 scanned outside the scanned image area of the x-ray detector scan area 115.

Figure 3:
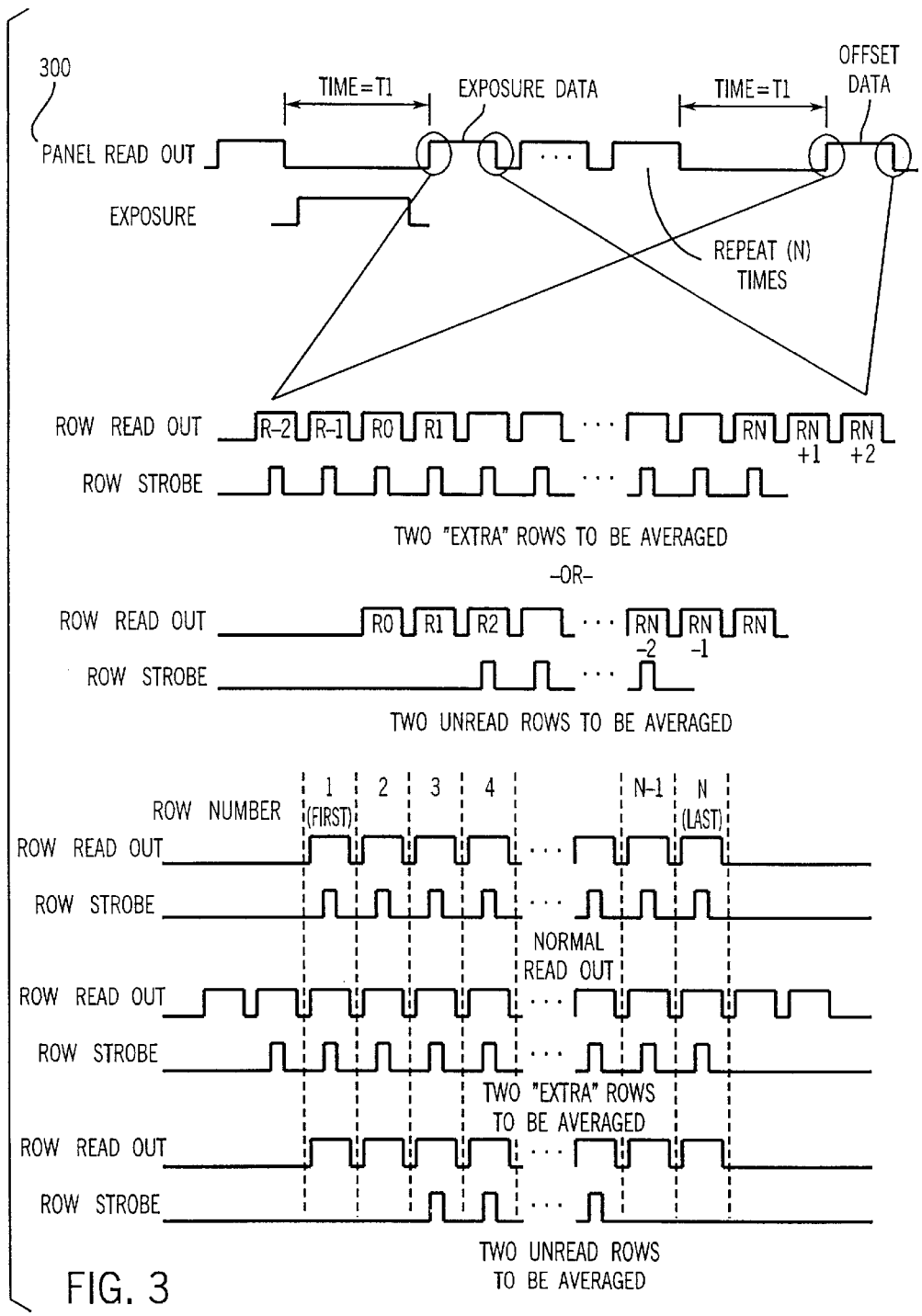
FIG. 3 shows a wave diagram demonstrating a method for acquiring an image according to a preferred embodiment of the present invention.

In step 230, the image adjustment module 150 receives x-ray image data from the image acquisition module 140. The image includes the additional rows dedicated to offset correction at the beginning and end of the image scan. The image adjustment module 150 analyzes the image on a pixel by pixel basis, according to row and column. In step 240, the image adjustment module 150 calculates the image data value for a pixel 410 in the image. For each pixel, the image data value (ID) is equal to the exposure data value (ED) from the image minus the charge retention offset data value (CR) from the "dark" image minus the calculated photoconductive offset data value (PC) from the offset correction rows 510, 610 (or $ID_{ij} = ED_{ij} - CR_{ij} - PC_{ij}$). In the calculation, i represents the row 430 index into the image and j represents the column 420 index into the image. The calculated photoconductive offset data value for each pixel 410 i in a given column 420 j is $((R_N - R_i)/R_N) * \frac{1}{2}((R-2)_e + (R-1)_e - (R_N+1)_e - (R_N+2)_e - (R-2)_o + (R_N+1)_o + (R_N+2)_o)$, where $(R-2)_e$ represents the signal measured in the expose frame for pixel (-2,j), and $R_N$ and $R_i$ are row numbers. The subscript "e" refers to the expose frame, and the subscript "o" refers to the offset frame, as depicted in FIG. 3. The resulting image data values for each pixel in the image may be used to generate a digital display.

Thus, the present invention provides a fairly simple solution to what has become a serious degradation issue for solid state x-ray detectors. The method and apparatus for measuring and correcting the offset induced by photo-conductive FETs in a solid state x-ray detector may improve the design of new medical diagnostic imaging systems and may preserve existing medical diagnostic imaging systems through offset correction. The present invention may be easily implemented and does not necessarily require a change to existing hardware.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for generating a medical diagnostic image acquired by a detector in a medical diagnostic imaging system comprising:

exposing a detector to an energy source to form an exposed detector section including an exposed patient subsection;

measuring at least first and second data sets generated by the detector, one of said first and second data sets being representative of at least a portion of said exposed detector section outside said exposed patient subsection and one of said first and second data sets being representative of at least a portion of said exposed patient subsection; and generating a medical diagnostic image based on said exposed patient subsection and a relation between said first and second data sets.

2. The method of claim 1 wherein said step of exposing a detector to an energy source comprises exposing said detector to x-ray energy.

3. The method of claim 1 wherein said first and second data sets comprise an exposure data set and a correction data set.

4. The method of claim 3 wherein said step of measuring at least first and second data sets comprises measuring said at least a portion of said exposed detector section outside said exposed patient subsection for said correction data set and measuring said at least a portion of said exposed patient subsection for said exposure data set.

5. The method of claim 3 wherein said step of generating said medical diagnostic image comprises subtracting a value from said correction data set from a corresponding value in said exposure data set.

6. The method of claim 1 wherein said step of generating said medical diagnostic image comprises subtracting a value from said first data set from a corresponding value in said second data set.

7. The method of claim 1 wherein said step of generating a medical diagnostic image comprises activating pixels in a digital display according to said measurements in said first and second data sets.

8. The method of claim 3 wherein said correction data set includes a measure of Field Effect Transistor photo-conductive effects.

9. The method of claim 1 wherein said step of measuring at least first and second data sets comprises said first data set being representative of at least a portion of said exposed detector section outside said exposed patient subsection and said second data set being representative of at least a portion of said exposed patient subsection.

10. The method of claim 9 further comprising measuring at least a third data set being representative of at least a second portion of said exposed detector section outside said exposed patient subsection.

11. A medical diagnostic imaging system, comprising:

a detector for detecting an energy pattern emanating from a patient; said detector having an array of discrete collecting elements storing charge representative of an amount of detected energy both from said patient and outside said patient;

an image acquisition module scanning a charge stored on said collecting elements; and said image acquisition module scanning said collecting elements during a first pass to obtain data representative of the intrinsic energy characteristic from an unexposed detector and during a second pass to obtain both exposure data representative of an energy pattern from said patient and correction data representative of an energy pattern of said detector from outside said patient.

12. The system of claim 11 further comprising:

an image adjustment module correcting said exposure data using said correction data to minimize the effect of said energy characteristic of said detector.

13. The system of claim 11 wherein said detector further comprises:

an array of Field Effect Transistors switchably interconnecting said collecting elements and said image acquisition module.

14. The system of claim 13 wherein said energy characteristic of said detector includes Field Effect Transistor photo-conductive effects.

15. The system of claim 11 wherein said collecting elements comprise photodiodes.

16. The system of claim 11 wherein said energy pattern is an x-ray energy pattern.

* * * * *